US00PP36725P2

(12) United States Plant Patent
Hofmann

(10) Patent No.: US PP36,725 P2
(45) Date of Patent: Jun. 3, 2025

(54) ***HELIOTROPIUM* PLANT NAMED 'INHELAROPU'**

(50) Latin Name: *Heliotropium arborescens*
Varietal Denomination: INHELAROPU

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GmbH & Co. KG, Gensigen (DE)

( * ) Notice: Subject to any disclaimer, the term of this patent is extended or adjusted under 35 U.S.C. 154(b) by 0 days.

(21) Appl. No.: 18/755,369

(22) Filed: Jun. 26, 2024

(51) Int. Cl.
*A01H 5/02* (2018.01)
*A01H 6/00* (2018.01)

(52) U.S. Cl.
USPC ..... Plt./438

(58) Field of Classification Search
USPC ..... Plt./438
CPC ..... A01H 5/02; A01H 5/00; A01H 6/00
See application file for complete search history.

(56) References Cited

PUBLICATIONS

Hullett, Stunning New Varieties at Proven Winners Open House 2024, retrieved on Sep. 30, 2024 at https://www.greenhousegrower.com/crops/stunning-new-varieties-at-proven-winners-open-house/#slide=167880-167879-15, one page. (Year: 2024).*
Missouri Botanical Garden retrieved on Oct. 2, 2024 at https://www.missouribotanicalgarden.org/PlantFinder/PlantFinderDetails.aspx?kempercode=a513, 2 pp. (Year: 2024).*
Proven Winners, Aromagica Purple Heliotrope, retrieved on Sep. 30, 2024 at https://www.provenwinners.com/plants/heliotropium/aromagica-purple-heliotrope-heliotropium-arborescens, 4 pp. (Year: 2024).*

* cited by examiner

*Primary Examiner* — June Hwu
(74) *Attorney, Agent, or Firm* — C. Anne Whealy

(57) ABSTRACT

A new and distinct cultivar of *Heliotropium* plant named 'INHELAROPU', characterized by its upright to somewhat outwardly spreading and mounding plant habit; relatively vigorous growth habit and relatively rapid growth rate; freely branching habit; dense and bushy plant form; early and freely flowering habit; relatively large inflorescences with numerous flowers; fragrant violet-colored flowers with white-colored centers; and good garden performance and relative tolerance to low temperature conditions.

2 Drawing Sheets

Figure 1:
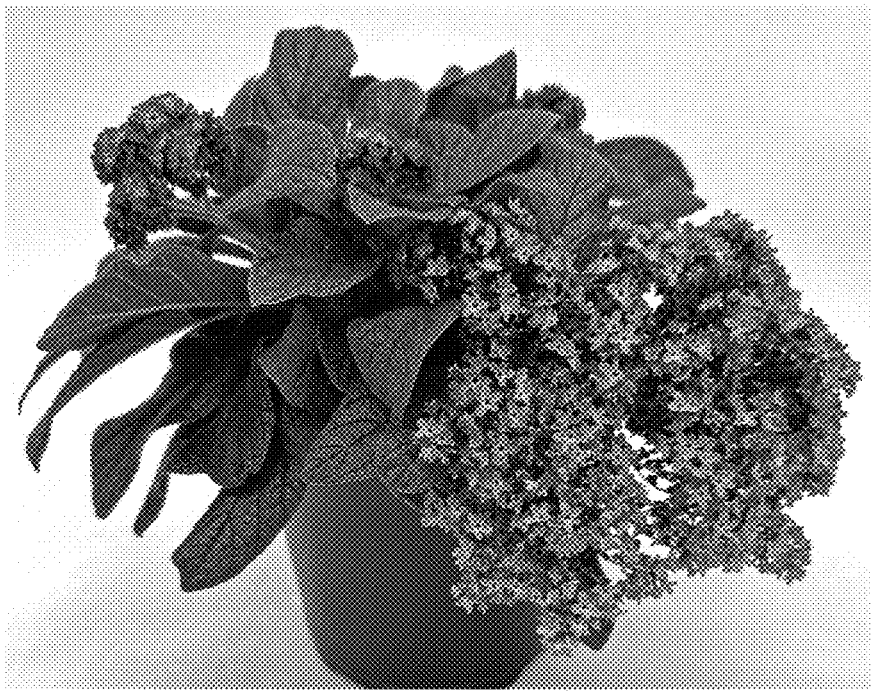

Botanical designation: *Heliotropium arborescens*.
Cultivar denomination: 'INHELAROPU'.

BACKGROUND OF THE INVENTION

The present invention relates to a new and distinct cultivar of *Heliotropium* plant, botanically known as *Heliotropium arborescens*, commonly referred to as Heliotrope and hereinafter referred to by the name 'INHELAROPU'.

The new *Heliotropium* plant is a product of a planned breeding program conducted by the Inventor in Heidesheim, Germany. The objective of the breeding program is to create new upright, freely-branching and early flowering *Heliotropium* plants with attractive leaves and flowers and low temperature performance.

The new *Heliotropium* plant originated from a cross-pollination conducted by the Inventor during the summer of 2012 of *Heliotropium arborescens* 'Incense', not patented, as the female, or seed, parent with a proprietary selection of *Heliotropium arborescens* identified as code number H10-1001-10, not patented, as the male, or pollen, parent. The new *Heliotropium* plant was discovered and selected by the Inventor as a single flowering plant from within the progeny of the stated cross-pollination in a controlled greenhouse environment in Heidesheim, Germany during the spring of 2013.

Asexual reproduction of the new *Heliotropium* plant by vegetative terminal cuttings in Heidesheim, Germany since June 2013 has shown that the unique features of this new *Heliotropium* plant are stable and reproduced true to type in successive generations.

SUMMARY OF THE INVENTION

Plants of the new *Heliotropium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INHELAROPU'. These characteristics in combination distinguish 'INHELAROPU' as a new and distinct *Heliotropium* plant:

1. Upright to somewhat outwardly spreading and mounding plant habit.
2. Relatively vigorous growth habit and relatively rapid growth rate.
3. Freely branching habit; dense and bushy plant form.
4. Early and freely flowering habit.
5. Relatively large inflorescences with numerous flowers.
6. Fragrant violet-colored flowers with white-colored centers.

7. Good garden performance and relatively tolerant to low temperature conditions.

Plants of the new *Heliotropium* can be compared to plants of the female parent, 'Incense'. Plants of the new *Heliotropium* differ primarily from plants of 'Incense' in the following characteristics:

1. Plants of the new *Heliotropium* are taller than plants of 'Incense'.
2. Plants of the new *Heliotropium* have smaller leaves than plants of 'Incense'.
3. Plants of the new *Heliotropium* are more tolerant to low temperature conditions than plants of 'Incense'.
4. Plants of the new *Heliotropium* are easier to propagate than plants of 'Incense'.

Plants of the new *Heliotropium* can be compared to plants of the male parent selection. Plants of the new *Heliotropium* differ primarily from plants of the male patent selection in the following characteristics:

1. Plants of the new *Heliotropium* are taller than plants of the male patent selection.
2. Plants of the new *Heliotropium* are more upright than and not as trailing as the male patent selection.
3. Plants of the new *Heliotropium* flower one week earlier than plants of the male patent selection.
4. Plants of the new *Heliotropium* have darker violet-colored flowers than plants of the male patent selection.

Plants of the new *Heliotropium* can be compared to plants of *Heliotropium arborescens* 'INHELMISKY', not patented. In side-by-side comparisons, plants of the new *Heliotropium* differ from plants of 'INHELMISKY' in the following characteristics:

1. Plants of the new *Heliotropium* are taller than and not as compact as plants of 'INHELMISKY'.
2. Plants of the new *Heliotropium* have stronger and sturdier lateral branches than plants of 'INHELMISKY'.
3. Plants of the new *Heliotropium* have larger leaves than plants of 'INHELMISKY'.
4. Plants of the new *Heliotropium* have larger inflorescences with larger flowers than plants of 'INHELMISKY'.

BRIEF DESCRIPTION OF THE PHOTOGRAPHS

The accompanying colored photographs illustrate the overall appearance of the new *Heliotropium* plant showing the colors as true as it is reasonably possible to obtain in colored reproductions of this type. Colors in the photographs may differ slightly from the color values cited in the detailed botanical description which accurately describe the colors of the new *Heliotropium* plant.

The photograph on the first sheet (FIG. 1) is a side perspective view of a typical flowering plant of 'INHELAROPU' grown in a container.

Figure 2:
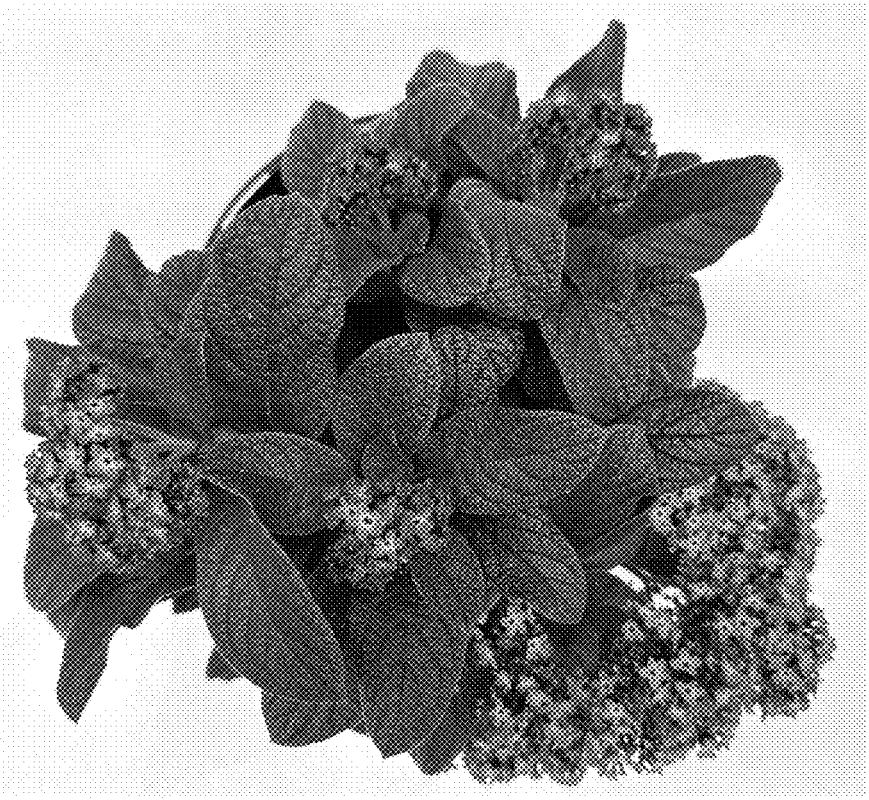

The photograph on the second sheet (FIG. 2) is a top perspective view of a typical flowering plant of 'INHELAROPU'.

DETAILED BOTANICAL DESCRIPTION

The aforementioned photographs and following observations and measurements describe plants grown during the winter in 10.8-cm containers in a glass-covered greenhouse in Loudon, New Hampshire and under cultural practices typical of commercial *Heliotropium* production. During the production of the plants, day and night temperatures averaged 18° C. High pressure sodium supplemental lighting was provided when ambient light levels were below 150 w/m$^2$. Plants were pinched one time and were 11.5 weeks from planting rooted cuttings when the photographs were taken and 12.5 weeks from planting rooted cuttings when the detailed description was taken. In the following description, color references are made to The Royal Horticultural Society Colour Chart, 2015 Edition, except where general terms of ordinary dictionary significance are used.

Botanical classification: *Heliotropium arborescens* 'INHELAROPU'.

Parentage:

*Female, or seed, parent.*—*Heliotropium arborescens* 'Incense', not patented.

*Male, or pollen, parent.*—Proprietary selection of *Heliotropium arborescens* identified as code number H10-1001-10, not patented.

Propagation:

*Type.*—By vegetative terminal cuttings.

*Time to initiate roots, summer.*—About two weeks at temperatures about 24° C.

*Time to initiate roots, winter.*—About 18 days at temperatures about 20° C.

*Time to produce a rooted young plant from unrooted cuttings, summer.*—About 16 to 21 days at temperatures about 24° C.

*Time to produce a rooted young plant from unrooted cuttings, winter.*—About 20 days at temperatures about 20° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial typically grown as a container and garden plant; upright to somewhat outwardly spreading and mounding plant habit; vigorous growth habit and rapid growth rate.

*Branching habit.*—Freely basal branching with lateral branches potentially developing at every node; bushy and dense appearance.

*Plant height.*—About 17 cm.

*Plant width.*—About 31 cm.

*Lateral branch description.*—Length: About 12 cm. Diameter: About 5 mm to 6 mm. Internode length: About 9 mm to 14 mm. Strength: Strong, sturdy; flexible. Aspect: Mostly upright to about 45° from vertical; distally, curving upright. Texture and luster: Densely pubescent; slightly glossy. Color, developing and developed: Close to 144A.

Leaf description:

*Arrangement.*—Whorled; simple.

*Length.*—About 10.5 cm to 11.25 cm.

*Width.*—About 4 cm to 4.5 cm.

*Shape.*—Elliptic.

*Apex.*—Bluntly acute with short cuspidate tip; curving downward with development.

*Base.*—Cuneate to attenuate.

*Margin.*—Entire, slightly undulate.

*Texture and luster, upper surface.*—Pubescent; velvety; somewhat glossy.

*Texture and luster, lower surface*.—Mostly glabrous with pubescence along veins and margins; slightly glossy.

*Venation pattern*.—Pinnate.

*Color*.—Developing leaves, upper surface: Close to 137A. Developing leaves, lower surface: Close to 137B. Fully expanded leaves, upper surface: Close to between 147A and N189A; proximal midvein, close to between 144A and 146A; distal midvein and lateral venation, close to between 147A and N189A. Fully expanded leaves, lower surface: Close to 147A; proximal midvein, close to 144A; distal midvein and lateral venation, close to 146A.

*Petioles*.—Length: About 1.2 cm to 1.4 cm. Diameter: About 2 mm by 3 mm. Strength: Moderately strong; flexible. Texture and luster, upper and lower surfaces: Pubescent; semi-glossy. Color, upper and lower surfaces: Close to 144A. Color, lower surface: Close to 146B to 146C.

Flower description:

*Flower arrangement and shape*.—Single actinomorphic salverform flowers arranged on relatively large and dense terminal helicoid cymes; three to four cymes per stem apex; freely flowering habit with numerous flowers continuously developing per inflorescence; flowers face mostly upright to outwardly to curling backwards depending on position on helicoid cymes; flowers sessile.

*Fragrance*.—Fragrant; pleasant, fresh; typical of Heliotropes.

*Natural flowering season*.—Early flowering habit, plants begin flowering about seven weeks after planting rooted cuttings; plants flower from late spring until the autumn in the garden in New Hampshire.

*Flower longevity*.—Depending on temperature, individual flowers last about three to seven days on the plant; flowers persistent.

*Flower buds*.—Length: About 2 mm. Diameter: About 1.5 mm. Shape: Oblong. Texture and luster: Pubescent; matte. Color: Distally, close to N88A and proximally, close to 144A.

*Inflorescence height*.—About 4.5 cm to 5 cm.

*Inflorescence diameter*.—About 5 cm to 6.5 cm.

*Flower diameter*.—About 6 mm to 7.5 mm.

*Flower length* (*depth*).—About 5 mm to 6 mm.

*Flower throat diameter*.—About 1.25 mm to 1.5 mm.

*Flower tube length*.—About 3 mm to 4 mm.

*Flower tube diameter, proximally*.—About 1 mm.

*Petals*.—Quantity and arrangement: Five petals in a single star-shaped whorl fused at the base into a slender tube. Petal lobe length (from throat): About 3 mm. Petal lobe width: About 3 mm. Petal lobe shape: Broadly ovate. Petal lobe apex: Bluntly acute. Petal lobe margin: Entire to finely crenate; ruffled and undulate. Petal lobe texture and luster, upper surface: Smooth, glabrous; velvety; slightly glossy. Petal lobe texture and luster, lower surface: Pubescent; matte. Throat texture and luster: Smooth, glabrous; matte. Tube texture and luster: Pubescent; matte. Color: When opening, upper surface: Close to N88A. When opening, lower surface: Close to N88A to N88B. Fully opened, upper surface: Close to N88A to N88B; towards the throat, close to NN155C to NN155D; venation, close to N88A to N88B; color becoming closer to N88B with subsequent development. Fully opened, lower surface: Close to N88B; venation, close to N88B; color becoming closer to N88C with subsequent development. Flower throat (inside): Distally, close to NN155C to NN155D and proximally, close to 144D; venation, close to 144D. Flower tube (outside): Close to N88B to N88C; venation, close to N88B to N88C.

*Sepals*.—Quantity and arrangement: Five sepals in a single star-shaped whorl fused at the base. Length: About 3 mm. Width: About 1 mm. Shape: Lanceolate. Apex: Acute. Margin: Entire. Texture, upper surface: Mostly glabrous with pubescence along margins. Texture, lower surface: Pubescent. Color: When opening and fully developed, upper surface: Close to 144A. When opening and fully developed, lower surface: Close to 144A.

*Peduncles*.—Length: About 1.25 cm to 2 cm. Width: About 1 mm to 2 mm. Strength: Strong; flexible. Angle: Upright to about 45° from lateral stem axis. Texture: Densely pubescent. Color: Close to 146A.

*Reproductive organs*.—Stamens: Quantity per flower: About five; adnate to the throat. Filament length: Less than 0.5 mm. Filament color: Close to 144A. Anther length: About 1 mm. Anther shape: Oblong. Anther color: Close to 144A to 144B. Pollen amount: Scarce. Pollen color: Close to 158C. Pistils: To date, pistil development has not been observed on plants of the new *Heliotropium*.

*Seeds and fruits*.—To date, seed and fruit production has not been observed on plants of the new *Heliotropium* plant.

Pathogen & pest resistance: To date, plants of the new *Heliotropium* have not been noted to be resistant to pathogens and pests common to *Heliotropium* plants.

Garden performance: Plants of the new *Heliotropium* have exhibited good garden performance and to be tolerant to rain, wind and temperatures ranging from about 5 C to about 45° C.

It is claimed:

1. A new and distinct *Heliotropium* plant named 'INHELAROPU' as herein illustrated and described.

* * * * *